United States Patent [19]

Caizza et al.

[11] Patent Number: 5,512,050
[45] Date of Patent: Apr. 30, 1996

[54] NEEDLE ASSEMBLY WITH COLLAPSIBLE AND RETRACTABLE SHEATH

[75] Inventors: Richard J. Caizza, Barry Lakes; Jon S. Bell, Midland Park, both of N.J.

[73] Assignee: Becton, Dickinson and Company, Franklin Lakes, N.J.

[21] Appl. No.: 309,278

[22] Filed: Sep. 20, 1994

[51] Int. Cl.⁶ .................................................. A61M 5/32
[52] U.S. Cl. ........................................ 604/263; 604/198
[58] Field of Search .................................... 604/263, 198, 604/192, 187, 110

[56] References Cited

U.S. PATENT DOCUMENTS

| | | | |
|---|---|---|---|
| 4,139,009 | 2/1979 | Alvarez | 128/218 |
| 4,664,654 | 5/1987 | Strauss | 604/198 |
| 4,795,432 | 1/1989 | Karczmer | 604/198 |
| 4,998,922 | 3/1991 | Kuracina et al. | 604/192 |
| 5,304,151 | 4/1994 | Kuracina | 604/198 |

*Primary Examiner*—John D. Yasko
*Attorney, Agent, or Firm*—Vincent A. Castiglione

[57] ABSTRACT

A needle cannula is surrounded by a collapsible sheath. The entire sheath can be retracted proximally on the needle cannula into a position where the distal tip of the needle cannula is visible to ensure optimal positioning and orientation for an injection. A spring may urge the entire sheath toward its distal position, and a lock may permit releasably retention of the entire sheath in its retracted proximal position.

12 Claims, 5 Drawing Sheets

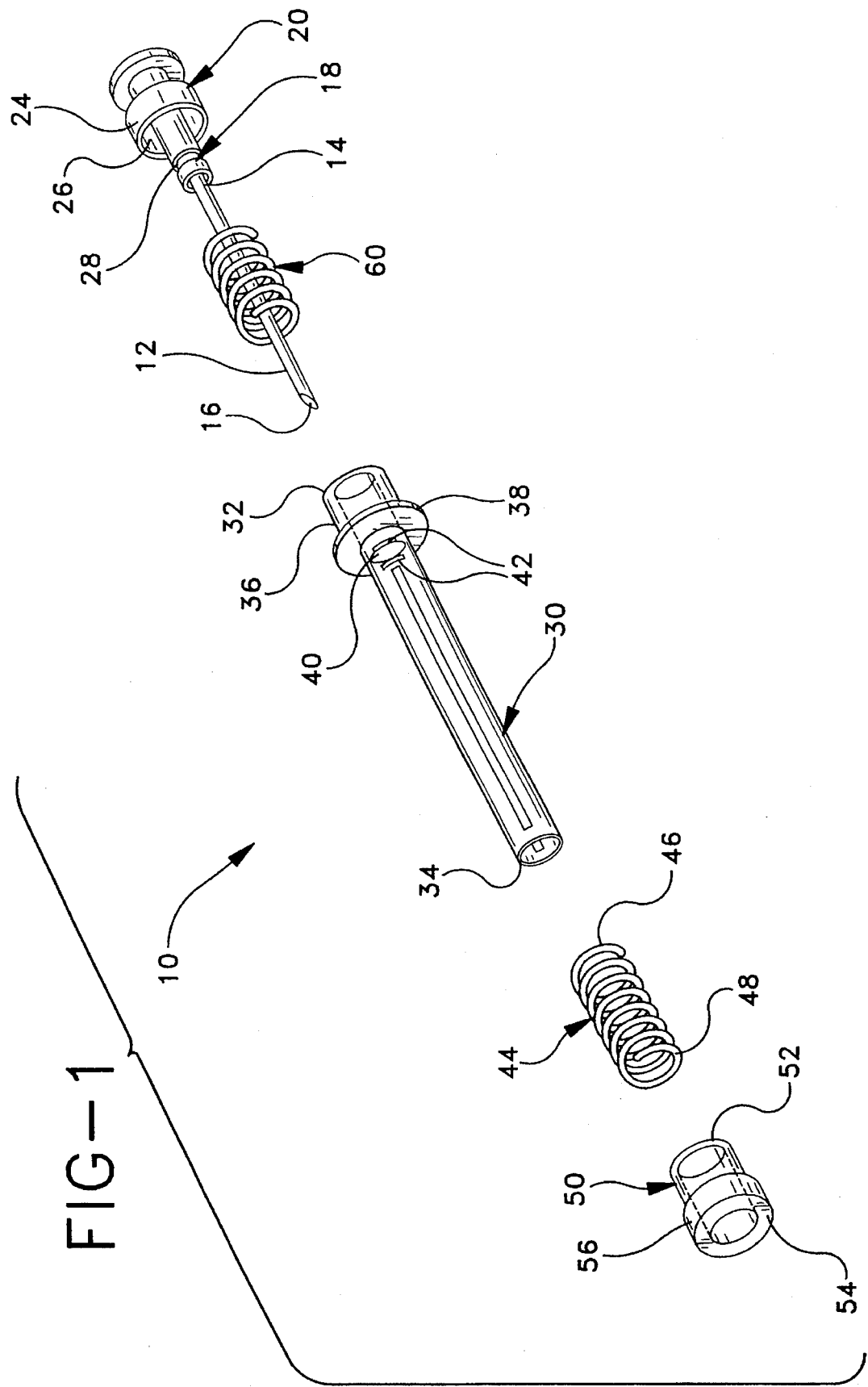

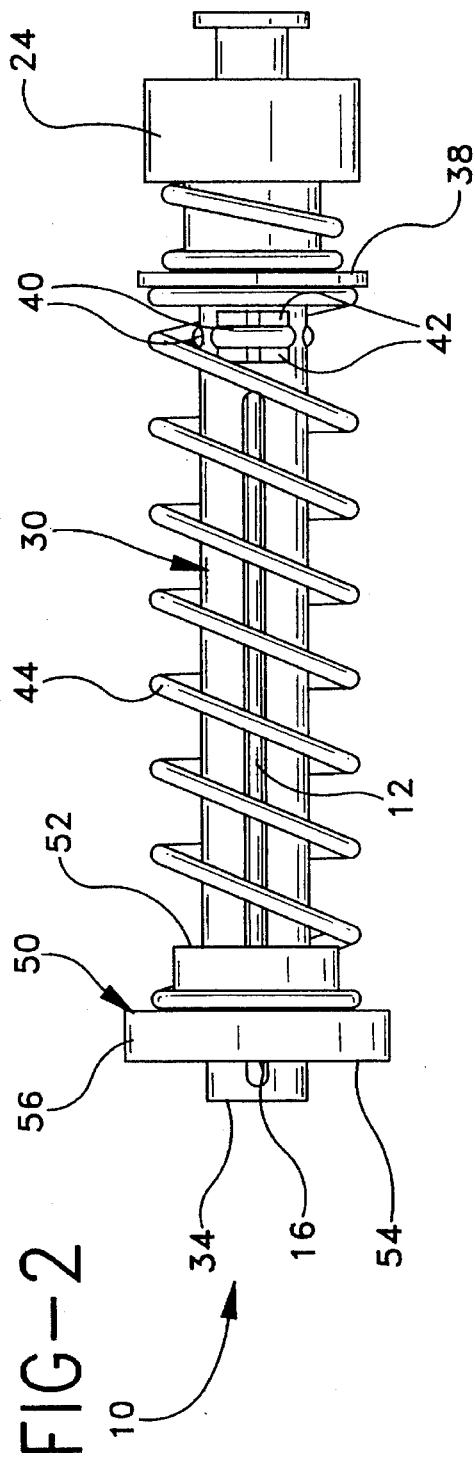
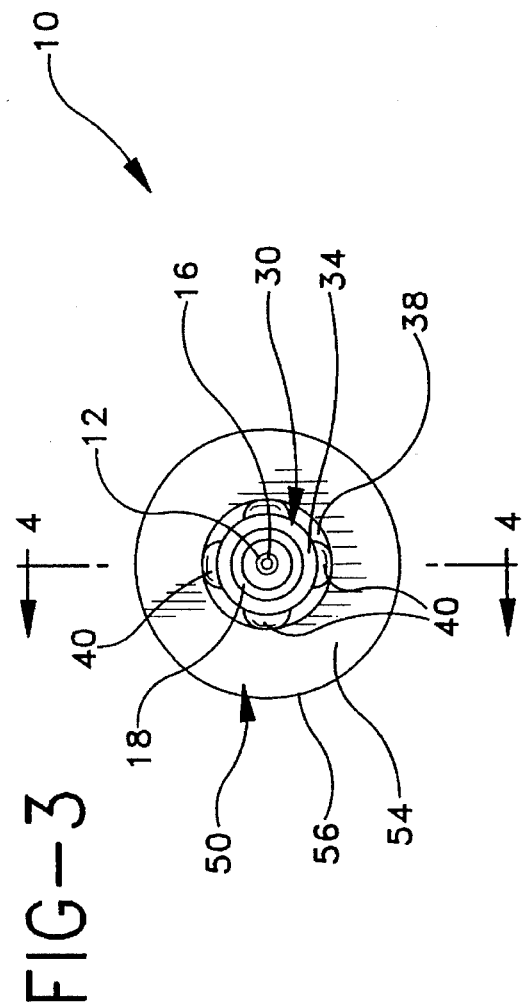

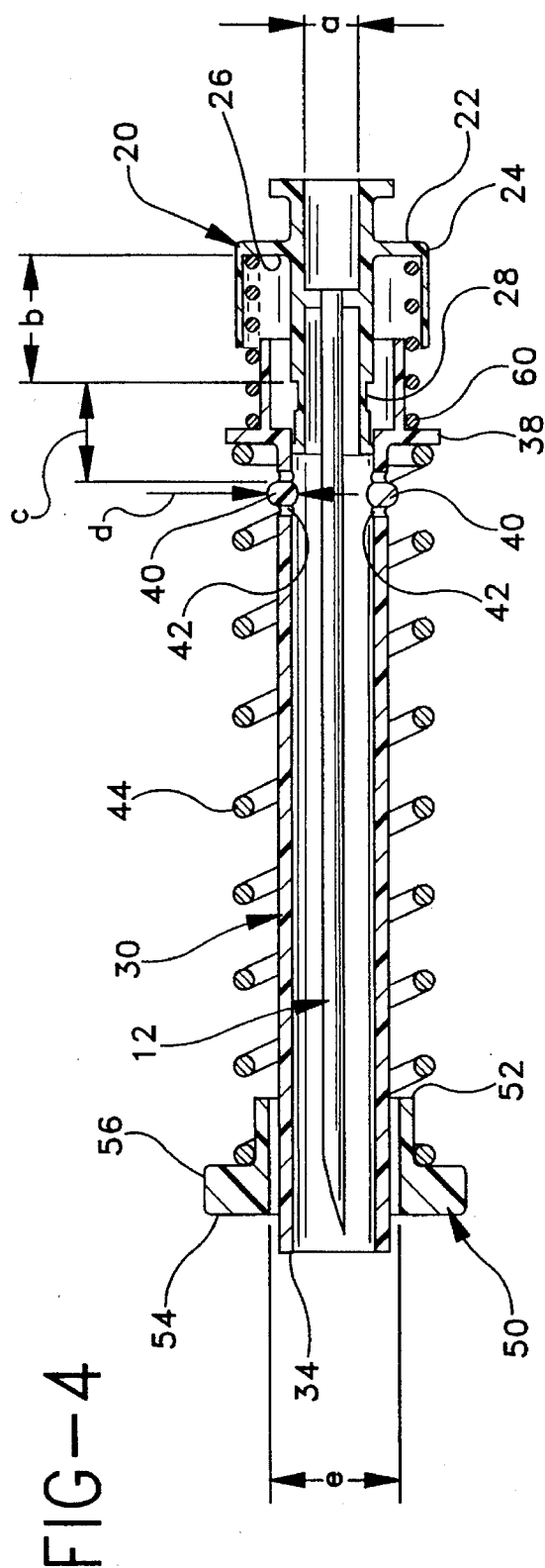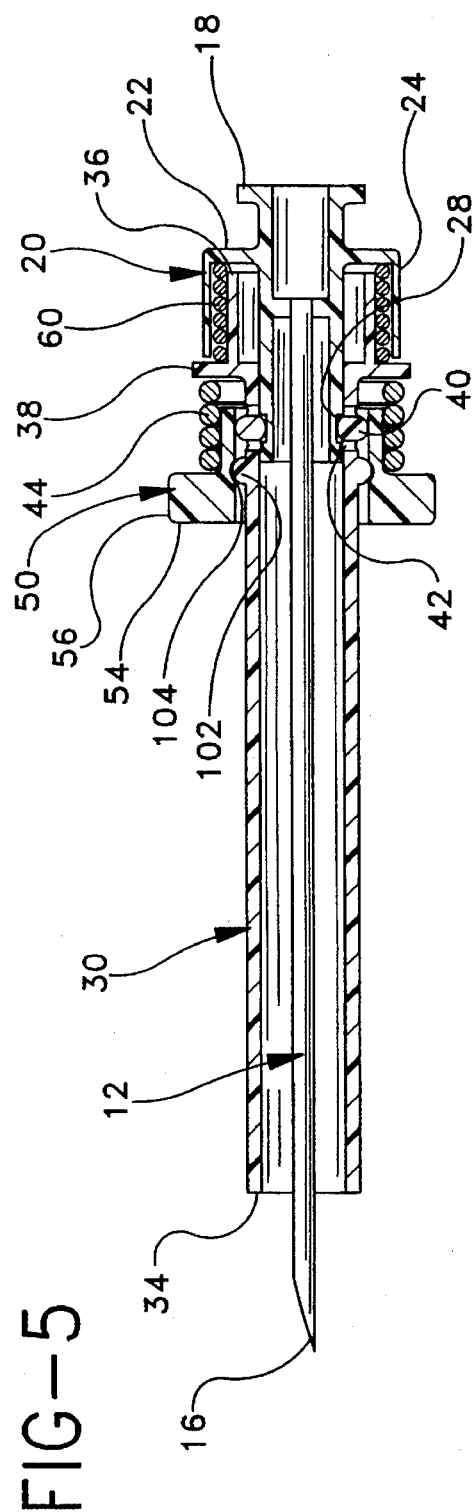

NEEDLE ASSEMBLY WITH COLLAPSIBLE AND RETRACTABLE SHEATH

BACKGROUND OF THE INVENTION

1. Field of the Invention

The invention relates to a needle assembly, and more particularly, to a needle assembly with a collapsible sheath that can be retracted to permit observation of the needle tip prior to injection.

2. Description of the Prior Art

A needle cannula includes opposed proximal and distal ends and a lumen extending therebetween. The proximal end of the prior art needle cannula is mounted to a hub for placing the lumen in communication with a medical instrument, such as a hypodermic syringe. Typically, the distal end of the prior art needle cannula is beveled to define a sharply pointed tip. Health care workers and patients can be stuck accidentally with the distal tip of a needle cannula. An accidental stick occurring prior to use of the needle cannula is painful and can cause infection. An accidental stick occurring after use of a needle cannula can further transmit disease.

Most prior art needle cannulas are provided with shields that are intended to reduce the risk of accidental sticks. Some prior art shields include a resiliently collapsible sheath that surrounds the needle cannula prior to use. In use, these sheaths extend distally beyond the needle cannula, and consequently will contact the skin of the patient prior to making an injection. The sheath expands radially and collapses axially as the needle cannula is moved toward and into the patient. The sheath then resiliently returns to an axially extended, radially contracted condition as the needle cannula is withdrawn from the patient. An example of a prior art collapsible sheath for a needle cannula is shown in U.S. Pat. No. 4,139,009. Prior art needle cannulas with collapsible sheaths present a false sense of security. Health care workers may assume that the covered needle is safely protected. However, any proximally directed force on the distal end of the sheath will expose the needle cannula and create the potential for accidental needle sticks.

More recent prior art includes a collapsible sheath that is closely surrounded by a coil spring. The proximal end of the coil spring is fixed near the proximal end of the sheath. However, remaining portions of the coil spring can be collapsed in a proximal direction independent of the sheath. The sheath functions substantially as in the above described U.S. Pat. No. 4,139,009 when the coil spring is collapsed. However, the coil spring can be released to expand axially and to closely surround the sheath. The coil spring is intended to prevent the radial expansion of the sheath that is required to axially collapse the sheath. Hence, the coil spring is intended to keep the sheath in its extended position. This combination of a sheath closely surrounded by a coil spring is shown in U.S. Pat. No. 4,998,922.

Prior art needle cannulas with retractable sheaths closely engaged by coil springs have several disadvantages. For example, the tip of the needle cannula generally is not visible prior to making an injection. As a result, it is difficult to precisely target a specific location for an injection. Additionally, many injections require a particular orientation of the bevel on the distal tip of the needle cannula. The sheath, however, covers the distal tip and prevents precise orientation of the bevel. Furthermore, many injections require the needle cannula to be aligned at an acute angle to the skin. In this orientation, an edge region of the sheath will contact the skin, and will tend to slide abrasively across the skin as the needle cannula is being advanced. This abrasion unnecessarily adds to the discomfort imposed upon the patient.

Co-pending U.S. patent application Ser. No. 08/309,372 entitled "Needle Assembly with Collapsible Sheath and Tip Guard" was filed by the inventors herein concurrently with this application, and relates to a needle assembly with a collapsible sheath and tip guard. The disclosure of this co-pending application is incorporated herein by reference. Co-pending application Ser. No. 08/309,372 provides several advantages over the prior art disclosed in U.S. Pat. No. 4,139,009 and U.S. Pat. No. 4,998,922, including the provision of a tip guard for positively preventing accidental needle sticks. While serving to provide a device for safe, reliable re-exposure of the needle cannula during use, there exists a further need for a device which will allow a user to readily observe the distal tip of the needle cannula prior to making an injection.

SUMMARY OF THE INVENTION

A needle assembly in accordance with the subject invention includes an elongate needle cannula having opposed proximal and distal ends. The distal end of the needle cannula may be beveled to define a sharp point. The proximal end of the needle cannula may be mounted to a hub that is selectively engageable with a medical instrument such as a hypodermic syringe. Alternatively, the needle cannula may be of the type utilized for blood collection and selectively engageable with a blood collection vessel or tube.

The needle assembly further includes a sheath surrounding the needle cannula. The sheath has opposed proximal and distal ends. The proximal end of the sheath may be mounted on or near the proximal end of the needle cannula for controlled axial movement of the entire sheath between a proximal position and a distal position. The sheath is sufficiently long to at least partially surround the distal end of the needle cannula when the sheath is in its distal position. However, the distal end of the needle cannula will be exposed when the entire sheath is retracted to its proximal position.

Biasing means may be provided for urging the entire sheath toward its distal position, and locking means may be provided for releasably holding the sheath in its proximal position. In addition to the above referenced axial movement, the sheath may be collapsed in response to proximally directed forces on the distal end of the sheath, such as those generated by an injection site such as the tissue of a patient during an injection. However the sheath may resiliently expand in the distal direction when the proximally directed forces have been removed.

The assembly may further include a safety spring which extends parallel to the sheath. The safety spring may have a proximal end mounted near the proximal end of the sheath and an opposed distal end. The distal end of the safety spring may extend toward the distal end of the needle cannula when the safety spring is expanded toward an unbiased condition. However, the entire safety spring may be contracted proximally such that the distal end of the safety spring is near the hub of the needle cannula.

A tip guard may be movably mounted on either the distal end of the spring or the distal end of the sheath, such as the tip guard disclosed in the above reference copending U.S. patent application Ser. No. 08/309,372, entitled "Needle Assembly with Collapsible Sheath and Tip Guard", filed by the inventors herein concurrently with this application and incorporated by reference herein.

BRIEF DESCRIPTION OF THE DRAWINGS

The invention will now be more fully described by way of reference to the appended drawings, wherein:

FIG. 1 is an exploded perspective view of a needle assembly with a collapsible and retractable sheath in accordance with the subject invention.

FIG. 2 is a side elevational view of the needle assembly of FIG. 1 illustrated in its assembled and shielded condition.

FIG. 3 is an end elevational view as viewed from the left side of FIG. 2.

FIG. 4 is a cross-sectional view taken along line 4—4 in FIG. 3.

FIG. 5 is a cross-sectional view similar to FIG. 4, but showing the needle assembly in a ready-to-use condition.

DETAILED DESCRIPTION OF THE PREFERRED EMBODIMENT

Figure 1A:
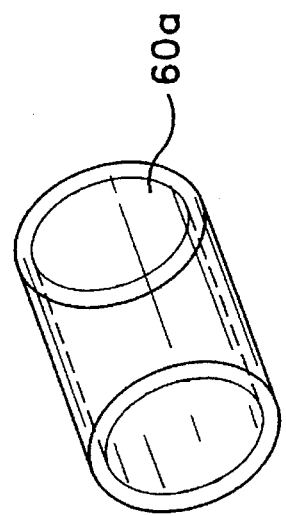
FIG. 1a is a perspective view of an alternate sheath-positioning means for the needle assembly of FIG. 1.
Figure 1B:
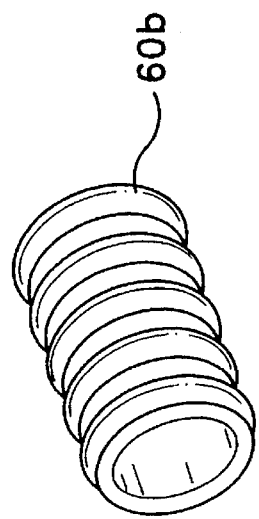
FIG. 1b is a perspective view of a second alternate sheath-positioning means for the needle assembly of FIG. 1.

Turning now to the drawings, wherein like numerals denote like components, a needle assembly in accordance with the subject invention is identified generally by the numeral 10 in FIGS. 1–6. Needle assembly 10 includes a needle cannula 12 having a proximal end 14 and an opposed sharply pointed distal end 16. Proximal end 14 of needle cannula 12 is securely mounted in a needle hub 18 for threaded interconnection with a luer collar of a hypodermic syringe. Alternately, as will be appreciated by those skilled in the art, the needle cannula 12 may be of the type utilized for blood collection purposes, and as such, the hub 18 may be appropriately configured for attachment to a blood collection tube or similar vessel. Other types of needle cannulae may be readily afforded with the features and advantages of the present invention.

Hub 18 includes a spring housing 20 having a radially aligned wall 22 and a distally projecting cylindrical outer wall 24. The radially aligned wall 22 and cylindrical outer wall 24 generally define a distally opening spring seat 26 surrounding the needle hub 18. As shown in FIG. 4, portions of hub 18 extending into spring seat 26 define an outside diameter "a". Hub 18 also includes an annular groove 28 spaced distally of the radial wall 22 of spring housing 20 by a distance "b".

Needle assembly 10 further includes a generally elongate sheath 30 with opposed proximal and distal ends 32 and 34, respectively, and generally configured to at least partially surround the needle cannula 12. Sheath 30 includes a tubular spring mounting wall 36 adjacent proximal end 32. Spring mounting wall 36 is dimensioned to telescope into spring seat 26 and to surround the needle hub 18. Sheath 30 further includes a spring driving wall 38 projecting radially from the distal end of spring mounting wall 36.

Sheath 30 may feature one or more circumferentially spaced deflectable locks 40 which are disposed distally of spring driving wall 38. The locks 40 may be configured or otherwise molded or defined in an integral manner with sheath 30. As illustrated in the figures, in order to prevent interference and insure proper seating of spring mounting wall 36 into spring seat 26, locks 40 may be spaced from annular groove 28 of hub 18, in the expanded state of sheath 30, by a distance "c" which is less than distance "b" between groove 28 and wall 22 of hub 18. Thus, locks 40 can align with groove 28 as the spring mounting wall 36 of sheath 30 is telescoped into seat 26 on spring housing 20 of hub 18. In one configuration, locks 40 may be formed as a raised nub or projection in the sheath 30, with a pair of short circumferentially extending slots 42 cut or otherwise formed through, on, or in sheath 30 on opposite axial sides of the lock 40. Slots 42 form a cantilevered structure about the locks which permit locks 40 to deflect into and out of grooves 28. Locks 40 define a radial thickness "d" as shown in FIG. 4 which is greater than the thickness of adjacent portions of sheath 30 to enable locking, as explained further herein.

Portions of collapsible sheath 30 intermediate locks 40 and distal end 34 are resiliently collapsible in response to proximally directed forces on distal end 34. These forces may be generated, for example, by urging the entire needle assembly 10 toward an injection site, or a withdrawal or collection site, such as a medication vial or a patient, for purposes of administering an injection or of removing bodily fluids, medication or the like.

Figure 6:
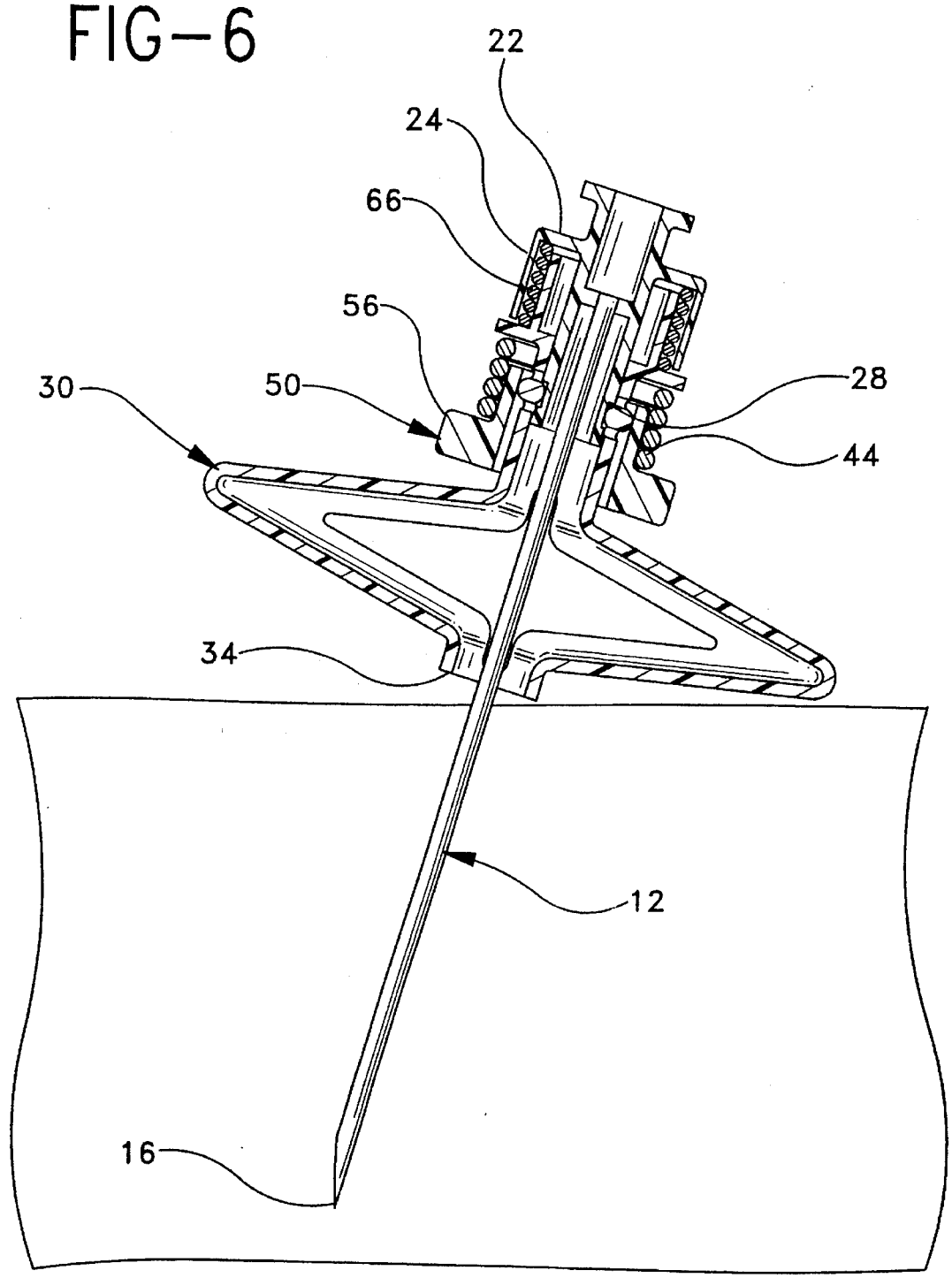
FIG. 6 is a cross-sectional view similar to FIGS. 4 and 5, but showing the needle assembly during use.

Needle assembly 10 further includes a safety spring 44 surrounding portions of sheath 30 between distal end 34 and spring driving wall 38. Safety spring 44 has opposed proximal and distal ends 46 and 48. Proximal end 46 of safety spring 44 abuts spring driving wall 38 of sheath 20. A generally tubular spring collar 50 is mounted at the distal end 48 of safety spring 44 and surrounds sheath 30 for slidable movement with distal end 48 of safety spring 44 along sheath 30. Collar 50 includes opposed proximal and distal ends 52 and 54 and an outwardly extending actuator flange 56 therebetween for manually moving collar 50 and safety spring 44. Collar 50 may define an inside diameter "e" dimensioned such that e<a+2d. Thus, collar 50 releasably engages outer circumferential portions of locks 40 on sheath 30 for frictionally retaining safety spring 44 in a proximally contracted condition as shown in FIGS. 5 and 6. Additionally, inside diameter "e" of collar 50 is sufficiently small (i.e., less than a +2d) to deflect locks 40 radially inwardly and into releasable engagement with groove 28 of needle hub 18. Thus, locks 40 simultaneously can engage both collar 50 and groove 28 of needle hub 18 depending upon the axial positions of sheath 30 and collar 50 relative to needle hub 18. Moreover, as will be further described hereinbelow, collar 50 can be released from its locked position relative to the needle hub 18 in order to resheath the needle cannula 12.

A sheath-positioning spring 60 surrounds spring mounting wall 36 of sheath 30 and projects proximally from spring driving wall 38 into spring seat 26. Sheath positioning spring 60 biases the entire sheath distally and toward a position where distal end 34 of sheath 30 surrounds distal end 16 of needle cannula 12, as shown in FIGS. 2–4. However, spring 60 permits the entire sheath to be telescoped proximally into a position where distal end 16 of needle cannula 12 is exposed and where locks 40 of sheath 30 align with annular groove 28 in needle hub 18.

Sheath-positioning spring 60 is illustrated in FIGS. 1 and 4–6 as a conventional coil spring. However, other configurations may be readily devised by those skilled in the art. For instance, in lieu of a coil spring, an elastomeric collar 60a or an elastomeric resilient bellows 60b may be provided as shown in FIGS. 1a and 1b, respectively. Moreover, for reasons to be more fully described hereinbelow, while not essential it is preferable that the spring constant ("k") associated with safety spring 44 be less than the spring constant associated with sheath positioning spring 60 or its substantial equivalents, such as resilient bellows 60b or elastomeric collar 60a, so as to enable efficient operation of the device with a minimum of effort on the part of a user.

As shown most clearly in FIGS. 2–4, sheath 30 may initially be disposed in an extended condition and in a distal position around needle cannula 12, such that distal end 34 of sheath 30 extends distally to or beyond distal tip 16 of needle cannula 12. In this condition, sheath-positioning spring 60 and safety spring 44 are at their maximum permitted expansions.

Needle assembly 10 is placed in the ready-to-use condition of FIG. 5 by manually urging collar 50 proximally. Initial proximal movement of collar 50 will compress safety spring 44 in the axial direction. As spring 44 approaches a fully compressed condition, further movement of collar 50 will move the entire sheath proximally. If the spring constant selected for spring 44 is less than the spring constant associated with spring 60, a steady, even force exerted by a user will cause spring 44 to compress before spring 60 will commence to compress. As those skilled in the art will realize, continued compression of spring 44 will cause the spring to stiffen. If the initial spring constant of spring 44 is duly selected, at some point intermediate full compression of spring 44, its spring constant will approach that associated with spring 60 so as to cause spring 60 to begin compressing. Thus, without requiring a user to have to alter the force applied upon collar 50, sheath-positioning spring 60 will commence to be compressed and spring mounting wall 36 of sheath 30 will be telescoped into spring seat 26 of needle hub 18. Sufficient proximal movement will frictionally retain collar 50 over locks 40 and will resiliently deflect locks 40 into groove 28. It will be understood, of course, that the spring constants for springs 44 and 60 need not be unequal, and that they may be selected as need or desire dictate, the locking operation of the device being otherwise identical.

To assist in the retention of collar 50, protrusions or other formations 102 may be molded or otherwise formed on the sheath 30, preferably distally of locks 40. The protrusions may be configured to mate with indentations or like formations 104 molded or otherwise formed on collar 50. See FIG. 5. In addition, as explained below, it will be understood that protrusions 102/indentations 104 may be configured for self-release upon termination of an injection. Thus, needle assembly 10 will be releasably retained in a ready-to-use condition, as seen in FIG. 5, with distal tip 16 of needle cannula 12 being visible to enable proper alignment and positioning of tip 16.

Sheath 30 will collapse as shown in FIG. 6 in response to a proximally directed force exerted on distal end 34 as needle cannula 12 is urged against the injection site (or withdrawal or collection site) such as a patient, a medication vial, an injection port, or the like for administering an injection (or for withdrawing or collecting bodily fluids, medicines or the like). Upon completion of an injection, sheath 30 will resiliently return toward the fully extended condition of FIG. 5. The user of the medical instrument to which needle assembly 10 is attached may then exert a distal force on outwardly extending flange 56 of collar 50 to overcome frictional forces between collar 50 and locks 40, and, if provided, to disengage indentations 104 from protrusions 102. When collar 50 moves distally beyond locks 40, the locks 40 will resiliently return to an undeflected condition free of groove 28. Collar 50 will then be propelled distally under forces exerted by safety spring 44, as safety spring 44 expands toward its unbiased condition. Simultaneously, sheath-positioning spring 60 will expand to move the entire sheath distally and into a position where distal end 34 of sheath 30 can surround distal end 16 of needle cannula 12 as shown in FIG. 4. Accidental needle sticks are at least partly prevented by sheath 30. Further protection from accidental sticks may be provided by cooperation between sheath 30 and safety spring 44 or by a tip guard as disclosed in the above referenced co-pending application. It will also be understood that if the dimensions of the components, inclusive of dimension "b", are appropriately chosen, the injection phase will cause the sheath 30 to move further proximally along the needle cannula so as to cause collar 50 to advance further proximally, resulting in the protrusions 102 being unseated from indentations 104. Thus, when the needle cannula 12 and sheath 30 are withdrawn from the injection site, an automatic resheathing of the needle cannula will result under the combined forces of springs 44 and 60, which can overcome the locking forces provided by locks 40 to expand sheath 30 following withdrawal of the needle cannula.

It will be appreciated and understood by those skilled in the art that further and additional forms of this invention may be realized without departing from the spirit and scope of the appended claims, it being understood that the invention is not to be limited to the specific embodiments shown.

What is claimed is:

1. A needle assembly comprising:
   a needle cannula having a proximal end and a distal end; and
   a sheath having opposed proximal and distal ends and disposed in surrounding relationship to said needle cannula, said sheath being selectively movable between a distal position where said distal end of said needle cannula is at least partially surrounded by said sheath and a proximal position where said distal end of said needle cannula is exposed, whereby said distal position of said sheath facilitates a user's observation of said distal end of said needle cannula prior to penetration in an injection site or withdrawal site and whereby said penetration urges said sheath into a collapsed condition; and a safety spring surrounding portions of said sheath and being selectively expandable and contractible in an axial direction, wherein portions of said safety spring are engageable with portions of said sheath such that said expansion of said safety spring urges said sheath toward an extended covering condition respective of the distal end of the needle cannula.

2. The needle assembly of claim 1, wherein said proximal end of said needle cannula comprises a needle hub, said proximal end of said sheath being mounted to said hub for movement of said sheath between said proximal and distal positions on said needle cannula.

3. The needle assembly of claim 2, wherein said sheath comprises locking means for releasably locking said sheath in said proximal position on said needle cannula.

4. The needle assembly of claim 1, further comprising a biasing spring for urging said sheath toward said distal position on said needle cannula.

5. The needle assembly of claim 4, wherein said sheath comprises releasable locking means for selectively locking said sheath in said proximal position on said needle cannula and against forces exerted by said biasing spring.

6. The needle assembly of claim 4, wherein said biasing spring is a coil spring.

7. The needle assembly of claim 1, wherein said safety spring comprises means for preventing collapsing of said sheath, and wherein said needle assembly further comprises retaining means for releasably retaining said safety spring in said contracted condition for permitting said collapsing of said sheath.

8. The needle assembly of claim 7, wherein said retaining means for retaining said safety spring in said contracted condition comprises said spring locking means for releasably locking said sheath in said proximal position.

9. A needle assembly comprising:
   a needle cannula having a distal end and an opposed proximal end comprising a needle hub;
   a sheath having opposed proximal and distal ends and disposed in at least partially surrounding relationship to said needle cannula, said proximal end of said sheath being mounted to said needle hub for movement between a proximal position and a distal position, said sheath further being selectively collapsible and extendible between an extended condition and a collapsed condition, said sheath defining a length in said extended condition for surrounding said distal end of said needle cannula when said proximal end of said sheath is in said distal position on said needle hub, said length of said sheath in said extended condition further being selected to expose said distal end of said needle cannula when said proximal end of said sheath is in said proximal position on said needle hub;
   a sheath positioning spring disposed between said sheath and said needle hub for biasing said sheath toward said distal position; and
   locking means disposed on said sheath for releasably locking said sheath in said proximal position and against biasing forces exerted by said sheath positioning spring, whereby said distal position of said sheath facilitates orientation of said distal end of said needle cannula prior to penetration in an injection site, and whereby said penetration urges said sheath into said collapsed condition.

10. The needle assembly of claim 9, further comprising a safety spring surrounding selected portions of said sheath and being selectively movable from an expanded condition where said safety spring prevents the collapsing of said sheath and a contracted condition where said safety spring permits the collapsing of said sheath.

11. The needle assembly of claim 10, further comprising a spring collar mounted to said safety spring for slidable movement along said sheath, said collar being releasably engageable with said sheath for releasably retaining said safety spring in said contracted condition.

12. The needle assembly of claim 11, wherein said needle hub includes an annular groove, said locking means of said sheath comprising at least one resiliently deflectable lock, said lock being dimensioned and disposed to be deflected inwardly into said groove by said collar, such that engagement of said lock and said groove releasably retains said sheath in said proximal position, and wherein engagement of said collar and said lock releasably retains said safety spring in said contracted condition.

* * * * *